US006654724B1

(12) United States Patent
Rubin et al.

(10) Patent No.: US 6,654,724 B1
(45) Date of Patent: Nov. 25, 2003

(54) SYSTEM FOR PROCESSING PHARMACEUTICAL DATA WHILE MAINTAINING PATIENT CONFIDENTIALLY

(75) Inventors: Daniel E. Rubin, Reading, MA (US); Bruce Higer, Chestnut Hill, MA (US); Matthew Glaser, Melrose, MA (US); James Rotsart, Attleboro, MA (US); Nicholas Leighton, Georgetown, MA (US)

(73) Assignee: Adheris, Inc., Woburn, MA (US)

( * ) Notice: Subject to any disclaimer, the term of this patent is extended or adjusted under 35 U.S.C. 154(b) by 0 days.

(21) Appl. No.: 09/249,075

(22) Filed: Feb. 12, 1999

(51) Int. Cl.[7] ............................................. G06F 17/60
(52) U.S. Cl. ............................................... 705/3; 705/2
(58) Field of Search ........................ 705/2, 3; 707/522, 707/9, 10, 104.1

(56) References Cited

U.S. PATENT DOCUMENTS

| | | |
|---|---|---|
| 3,921,196 A | 11/1975 | Patterson |
| 3,970,996 A | 7/1976 | Yasaka et al. |
| 4,766,542 A | 8/1988 | Pilarczyk |
| 4,835,372 A | 5/1989 | Gombrich et al. |
| 5,325,294 A | 6/1994 | Keene |
| 5,509,064 A | 4/1996 | Welner et al. |
| 5,597,995 A | 1/1997 | Williams et al. |
| 5,612,870 A | 3/1997 | Welner |
| 5,623,242 A | 4/1997 | Dawson, Jr. et al. |
| 5,664,109 A | 9/1997 | Johnson et al. |
| 5,689,247 A | 11/1997 | Welner |
| 5,737,539 A | 4/1998 | Edelson et al. |
| 5,754,938 A | 5/1998 | Herz et al. |
| 5,758,095 A | 5/1998 | Albaum et al. |
| 5,784,635 A * | 7/1998 | McCallum ................. 707/522 |
| 5,827,180 A | 10/1998 | Goodman |
| 5,832,488 A | 11/1998 | Eberhardt |

FOREIGN PATENT DOCUMENTS

EP     0 884 670 A1 * 12/1998

OTHER PUBLICATIONS

Herting et al., "Large Scale Database Scrubbing Using Object Oriented Software Components" Proceedings of AMIA Symposium, p. 508–512, Nov. 8, 1998.*

Neame, "Measures Implemented to Project Personal Privacy for an On–Line National Patient Index: A Case Study" Topics in Health Information Management Nov. 1996, pp. 18–25.*

Neame et al., "Measures Implemented to Project Personal Privacy for an On–Line National Patient Index: A Case Study" Topics In Health Information Management, Nov. 1996, abstract.*

* cited by examiner

Primary Examiner—M. Kemper
(74) Attorney, Agent, or Firm—Greenblum & Bernstein, P.L.C.

(57) ABSTRACT

A system is provided for processing data including patient identity information and pharmaceutical information. The system permits analysis of the pharmaceutical information to occur while maintaining the confidentiality of the patient identity information. The system includes a server and a data processor. The server stores the data and transmits the data to a data processor. Before transmitting the data, the server replaces the patient identity information with unique generic identification information. The data processor imports the data, including the substituted generic identification information, and analyzes the pharmaceutical information to obtain results. The data processor then exports the results along with the associated generic identification information back to the server. Upon receiving the results, the server supplements the generic identification information with the corresponding patient identity information so that the results are associated with the patient identity information corresponding to the substantive information that is the source of the results. However, the data being processed is not limited to pharmaceutical information. That is, the present invention has applications in numerous fields, such as law, finance or any other field that requires confidentiality.

25 Claims, 5 Drawing Sheets

SYSTEM FOR PROCESSING PHARMACEUTICAL DATA WHILE MAINTAINING PATIENT CONFIDENTIALLY

BACKGROUND OF THE INVENTION

1. Field of the Invention

The present invention relates to a system for processing pharmaceutical data. More particularly, the present invention pertains to a system that maintains the confidentiality of a patient's identity information associated with the pharmaceutical data being processed. However, the data being processed is not limited to pharmaceutical information. That is, the present invention has applications in numerous fields, such as law, finance or any other field that requires confidentiality.

2. Discussion of Background Information

Up until now, the issue of medical record confidentiality has not been adequately addressed. In order for health care providers to offer the highest level of patient care, it is essential to enlist the trust of patients, specifically with regard to the issue of protecting the confidentiality of any medical information provided in confidence by patients to health care providers. This would include prescription medication information provided to pharmacists.

Pharmacy-based medication compliance programs remind patients when their prescription, as written by their doctor, needs to be refilled and provide patients with information about medication usage, potential side effects, and precautions. Typically, such programs are implemented by providing patients with mailed communications from their local pharmacists at specific intervals during their prescription therapies (e.g., prior to refills coming due). Such pharmacy-based medication compliance programs have proven to be successful at increasing the rate that patients adhere to their physicians' prescribed instructions across multiple therapeutic categories. Some programs have demonstrated increases in compliance on the order of 50% or greater.

Due to the large volume of prescriptions being filled nowadays, pharmacists often need assistance in fulfilling administrative tasks, such as sending patient reminders, so the pharmacists have more time to devote to serving patients at the pharmacy. Thus, pharmacies frequently enlist the assistance of outside parties to implement compliance programs.

Compliance programs help patients to follow their physician's instructions. Without compliance programs, only about half of all prescriptions written each year are taken correctly. The other half are taken incorrectly, by patients who are "non-compliant" with their doctor's prescribed instructions. The term non-compliant is a catch-all phrase referring to any deviation from a prescribed pharmaceutical regimen, including: over-dosing/taking medication too frequently, taking medication at incorrect times of the day, under-dosing and periodic drug holidays, sharing prescribed medicines with others, mixing medicines inappropriately with alcohol, tobacco, certain foods, and other prescribed or over-the-counter remedies, and failing to fill or refill prescriptions altogether.

Taken in total, non-compliance in its many forms exacts a significant toll in unnecessary health care costs, lower quality of patient health, and even lost lives. Conservative estimates from academic researchers, government agencies, and health care industry experts indicate that each year, non-compliance with prescribed pharmaceutical regimens in the United States contributes to: between 6–10% of all hospital admissions; 125,000 deaths in the cardiovascular area alone; over 20 million lost working hours; and between $15–20 billion in avoidable health care costs.

Canada has non-compliance issues similar to those in the United States, and the problem has been studied there as well. In Canada, non-compliance with prescription medications is estimated to cost the health care system between $7 and $9 billion each year in direct and indirect costs. This makes prescription non-compliance one of Canada's largest and most expensive "disease" categories, equivalent to the total cost of coronary heart disease.

The problem of non-compliance is particularly severe in pharmaceutical therapies for chronic, long-term conditions such as hypertension, asthma, epilepsy, and hypercholesterolemia. The predominant form of non-compliant behavior in such long-term therapies is premature discontinuance (i.e., missed refills). In fact, several studies have shown that patient retention rates in long-term therapies decline to 50% over the first six to twelve months of therapy, regardless of the illness or patient setting.

Pharmacists are in perhaps the best position to help patients adhere to their doctor's prescription instructions. Pharmacists are trained to answer questions about prescriptions for their patients and they are always looking for ways to better communicate with their patients. Systems presently exist to facilitate this communication using modem and cost-effective methods that support and reinforce the efforts of today's busy pharmacists. However, such systems require that confidential prescription information be provided to the third parties that are implementing the services.

As previously stated, medication compliance programs often involve the use of outside parties by pharmacies to assist in the program implementation. In order to implement such programs, pharmacies are frequently required to provide patient prescription records to third parties for data processing and analysis. While the confidentiality of these records can be protected by contractual obligations between the pharmacy and the third party, the perception that patient confidentiality may be compromised could exist. Because of the significant health care value of pharmacy-based medication compliance programs, a need exists for a solution that allows pharmacies to implement compliance programs without any real or perceived violation of the confidentiality of patient prescription records.

SUMMARY OF THE INVENTION

Hence, an object of the invention is to respond to the public debate surrounding prescription record confidentiality issues. This object is achieved by allowing pharmacies to utilize third party services to help them implement medication compliance services for their patients without ever providing confidential patient-identifiable information to the third party. According to the present invention, patient-identifiable information contained in a patient prescription record is automatically replaced with a unique patient identification number, enabling pharmacies to generate an electronic file that can be provided to third party data processors to facilitate the use of medication compliance programs. The patient-identifiable information is re-united with the "patient-blinded" database files, used to generate communications from the pharmacist to the patient, within the pharmacy environment. Thus, the present invention enables pharmacies to address the serious health care problem of medication non-compliance in a manner that preserves the confidentiality of patients' private medical records.

A system is provided for processing data including specific identity information and substantive information. The system permits analysis of the substantive information to occur while maintaining the confidentiality of the specific identity information. The system includes a server and a data processor. The server stores the data and transmits the data to a data processor. Before transmitting the data, the server replaces the specific identity information with unique generic identification information. The data processor imports the data, including the substituted generic identification information, and analyzes the substantive information to obtain results. The data processor then exports the results along with the associated generic identification information back to the server. Upon receiving the results, the server supplements the generic identification information with the corresponding specific identity information so that the results are associated with the specific identity information corresponding to the substantive information that is the source of the results. The unique identification information may be a name and an address. A local system that supplies the data to the server may also be provided. Moreover, the results may be intervention types and timing and the server may receive the results and add the name and address to the results so that correspondence can be generated in accordance with the intervention types and timing for that name. The individual identity information is forwarded to a fulfillment house in a preferred embodiment.

According to another embodiment, a system is provided for processing data including specific identity information and substantive information. The system permits analysis of the substantive information to occur at a remote site while maintaining the specific identity information at a local site. The system includes a local server residing at the local site and an analyzing system. The local server stores the data and transmits the data to the remote site. The local server substitutes the specific identity information with unique generic identification information before transmitting. The analyzing system resides at the remote site and imports the data, including the substituted unique identification information, from the local site. The analyzing site analyzes the substantive information to obtain results and exports the results along with the associated generic identification information back to the local site. The generic identification information is combined with the specific identity information at the local site so that the results are associated with the specific identity information corresponding to the substantive information that is the source of the results.

The data may be transmitted via a T1 connection. Moreover, The specific identity information may include a patient's name and address.

According to another embodiment, a system is provided for processing data including specific identity information and substantive information. The system permits analysis of the substantive information to occur at a remote site while maintaining confidentiality of the specific identity information. The system includes a server residing at the remote site and an analyzing system. The server stores the data and transmits the data and substitutes the specific identity information with unique generic identification information before transmitting. The analyzing system also resides at the remote site and receives the transmitted data, including the substituted generic identification information. The analyzing system analyzes the substantive information to obtain results that are exported, along with the associated unique identification information, back to the server. The server supplements the generic identification information with the specific identity information so that the results are matched with the specific identity information corresponding to the substantive information that is the source of the results.

According to another embodiment, a method is provided for processing data, including specific identity information and substantive information. The system permits analysis of the substantive information to occur while maintaining the confidentiality of the specific identity information. The method includes storing the data; substituting the specific identity information with unique generic identification information; and transmitting the data, including the substituted generic identification information and the substantive information to a data processor. Subsequently, the data processor imports the data, including the substituted generic identification information, and analyzes the substantive information to obtain results; and exports the results along with the associated generic identification information back to the server. Subsequently, the server associates the generic identification information with the corresponding specific identity information so that the results are associated with the specific identity information corresponding to the substantive information that is the source of the results.

The method may also include the server transmitting the results to a fulfillment house. Moreover, the method may include the server processing the results and transmitting correspondence in accordance with the results. Preferably, the server cleans the data before transmitting the data to the data processor. The server cleans the data by removing undesired predetermined information from the data before transmitting the data to the data processor. The server and the data processor can be located at the same site or at different sites.

According to another embodiment, a method is provided for facilitating compliance while maintaining a patient's confidentiality within a pharmaceutical system including a plurality of local systems, a local server, a remote compliance system, and a fulfillment system. The method includes transferring the patient's identity information along with the patients prescription information from the plurality of local systems to the local server; substituting the patient's identity information with a unique generic ID at the local server; transferring the generic ID and prescription information to the remote compliance system; processing the prescription information, associated with the generic ID, and exporting intervention information, the generic ID, and a letter library to the local server; supplementing the generic ID with the patient's identity information at the local server; merging the export file, letter library and patient information to obtain fulfillment information; and transferring the fulfillment information to the fulfillment system to generate correspondence to be sent to the patients.

The supplementing may include storing the patient's identity information and the generic ID in a table residing on the local server. The replacing may include locating the unique ID in the table to find the corresponding patient's identity information. Preferably, the local server and the remote compliance system are located at the same site.

According to another embodiment, a computer data signal is provided. The signal enables data processing while maintaining confidentiality and includes three states. Th first state includes the substantive information and specific identity information. The second state includes the substantive information and a unique generic ID that anonymously represents the specific identity information. The third state includes analysis results of the substantive information, the generic ID, and the specific identity information represented by the generic ID. Consequently, analysis of the signal in the second state occurs without knowledge of the specific identity information, thus maintaining confidentiality of the specific identity information.

According to another embodiment, a medical data analysis preparation system is provided for processing prescription data including personal identity information and prescription information and for preventing access to the personal identity information by a data processor that analyzes the prescription information. The system includes a classification component that classifies records of the prescription data into the personal identity information and the prescription information while maintaining association of the personal identity information with the prescription information. The system also includes an anonymizing component that converts a predetermined record within the personal identity information to unique generic identification information associated with the prescription information. The system also includes a confidential data stripping component that removes all personal identity information from the prescription data other than the generic identification information. The system also includes a transmitting component that transmits the prescription information together with the associated generic identification information to the data processor. The system also includes a receiving component for receiving analysis results along with the associated generic identification information from the data processor. The system also includes an associating component that associates the generic identification information with corresponding personal identity information and converts the predetermined record back into the personal identity information. The system also includes an output component that outputs the analysis results together with the associated personal identity information. Preferably, the system also includes an intervention action component that converts the analysis results into intervention types and timing associated with the personal identity information and generates preformatted letters.

According to another embodiment, a system is provided for processing data including specific identity information and substantive information. The system permits analysis of the substantive information to occur while maintaining the confidentiality of the specific identity information. The system includes a server that stores the data and transmits the data. The server substitutes the specific identity information with unique generic identification information before transmitting. When the server receives results along with the associated generic identification information, the server associates the generic identification information with the corresponding specific identity information so that the results are associated with the specific identity information related to the substantive information that is the source of the results. The server may reside at a pharmacy.

BRIEF DESCRIPTION OF THE DRAWINGS

The invention is explained in greater detail below with reference to the noted plurality of drawings by way of non-limiting examples of preferred embodiments of the present invention, in which like reference numerals represent similar parts throughout the several views of the drawings, and wherein.

DETAILED DESCRIPTION OF THE PRESENT INVENTION

Although the present invention has applications in numerous fields, such as law, finance or any other field that requires confidentiality, the system will be described with respect to medicine, particularly a compliance program within a pharmacy environment.

Figure 1:
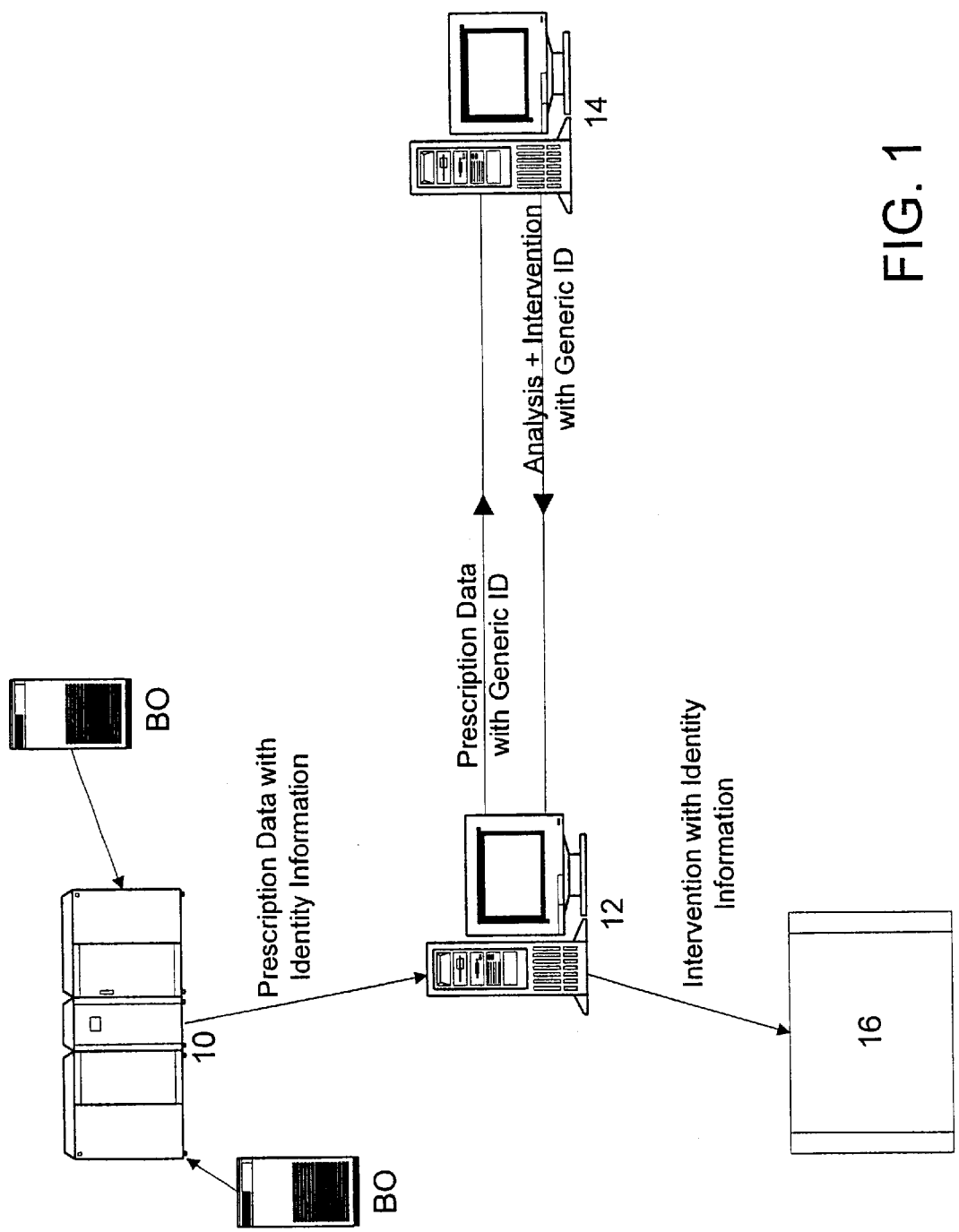
FIG. 1 shows an exemplary overall system in accordance with an aspect of the invention.

FIG. 1 shows an exemplary hardware architecture according to the present invention. Initially, a central mainframe computer 10 obtains data from branch offices BO. The mainframe is located at a pharmacy's central office and the branch offices represent the various stores within the pharmacy chain. The mainframe computer 10 typically periodically polls the branch offices to obtain the data, but any known manner for importing data may be employed. For example, the branch office computers may call into the mainframe computer 10 on a predetermined schedule, or upon the occurrence of predetermined events (e.g., a fixed number of data records are created). In a preferred embodiment the polling occurs weekly and the mainframe is an IBM. However, any mainframe or high-capacity computer (minicomputer, distributed system, or cluster) having an Internet protocol (e.g., TCP/IP stack) enabling file transfer (e.g., File Transfer Protocol (FTP)) capability can be utilized. Alternatively, the polling can occur at other intervals, such as daily or monthly. The mainframe 10 obtains the data via FTP in any known manner.

The mainframe 10 forwards the data to an on-site server 12, also located at the central office. The on-site server 12 is preferably a computer running at least one Pentium class processors. A second processor may be provided for redundancy. Moreover, the on-site server 12 runs an operating system, such as Microsoft Windows NT 4.0, in a mirror, i.e., on its own disk drive. Preferably, the on-site server also includes a RAID-5 or any similar array for data storage, access speed, and redundancy and a remote control board, such as a Compaq Remote Insight Board. The remote control board allows remote systems to control the on-site server 12 by permitting configuration and administrative interaction over Internet or WAN protocols. Finally, the server should be connected to a router. In a preferred embodiment, a Bay Networks ARN is employed. The router should have a serial interface.

The on-site server 12 processes the received data, categorizes patient identity data and prescription data, and substitutes certain patient identity information with a unique generic identification (ID), while removing other patient identity data from any prescription data transmitted. Details of the processing and substitution will be described below with respect to FIG. 2. The data, including the substituted unique generic ID, is then transferred to a data processing server 14 at a data processing center, preferably but not necessarily located remotely from the central office. The data processing server 14 has similar requirements to the on-site server 12, except that the data processing server 14 does not require a remote control board. For example, the server should also be connected to a router, such as a Bay Networks ARN having a serial interface.

It should be noted that an embodiment of the invention having restricted functionality includes only the on-site server and hardware and software structures therein, while more extended embodiments include the signals exchanged, the data processing center and/or fulfillment house as well.

Encryption can be provided for the data transfer. In a preferred embodiment, virtual private network technology is utilized to transmit the data. Typically, and in this case, virtual private networks (VPNs) "tunnel" their own protocol and packets within standard Internet IP packets. VPNware's VSU-10 is preferably employed. The VSU-10 increases throughput and provides hardware encryption. A VSU-10 should be connected to both the transmitting and receiving computer.

Once the data is received at the data processing server 14, the data is processed. A detailed description of exemplary processing is provided below with respect to FIGS. 4 and 5. After the data is processed, results are exported back to the on-site server 12. For example, the data processing server 14 may initiate the export, or the processed results may reside on the data processing server 14 until the on-site server 12 polls the data processing server. According to a preferred embodiment, all transfers between the on-site server 12 and the data processing server 14 are via T-1 lines. However, any transmission link may be substituted for the T-1 line, but preferable a wide band link (e.g., xDSL, frame relay, X.11, cable modem, etc.) is used. Moreover, the data may be transferred via tape transfer, modem or FTP. It should be noted that any of the transfers previously or subsequently described can be via any of those formats or any other known format for transferring data.

Once the results are received, the on-site server 12 replaces the unique generic ID with the original personal or patient identity information and forwards the results, along with the original identity information and intervention information, to a fulfillment house 16. The fulfillment house 16 receives the exported results via FTP from the on-site server 12. Preferably, the fulfillment house 16 also receives a pharmacy file that contains the address, phone number, pharmacy ID, and head pharmacist's name for each pharmacy in the compliance program. Each patient export record is linked to a pharmacy record enabling the fulfillment house 16 to merge the two files together so that every export record has a pharmacy address, phone number, and pharmacist associated with it. The link is created by cross referencing the pharmacy ID in the pharmacy file with the pharmacy ID in the exported results. Finally, the fulfillment house 16 generates correspondence in accordance with the results from the data processing server 14.

Exemplary data being transferred to the on-site server 12 from the mainframe 10 is shown in Table 1 and includes: a national drug code (NDC); the patient's name, address, phone number, date of birth (DOB), gender, and weight; insurance information; the pharmacist; the pharmacy filling the prescription; the prescription number; the type of illness; and information about the prescription itself. Not all of that information is necessarily transferred, but rather the preceding is a list of preferred data fields. Of course other information can be included. In a preferred embodiment, the NDC, patients name and address, pharmacy, and prescription number are required.

TABLE 1

Prescription Data Fields

| Personal Identity Fields | Substantive Information Fields | |
|---|---|---|
| Name | NDC | Refills prescribed |
| Address | DOB | Refills remaining |
| Phone Number | Gender | Refill No. |
| | Weight | Date Dispensed |
| | Insurance Info | Quantity dispensed |
| | Pharmacist | Price |
| | Pharmacy | Paid |
| | Prescription No. | Co-pay |
| | Illness | No. days dispensed |
| | Prescription Notes | Dosing Instr. |

Figure 2:
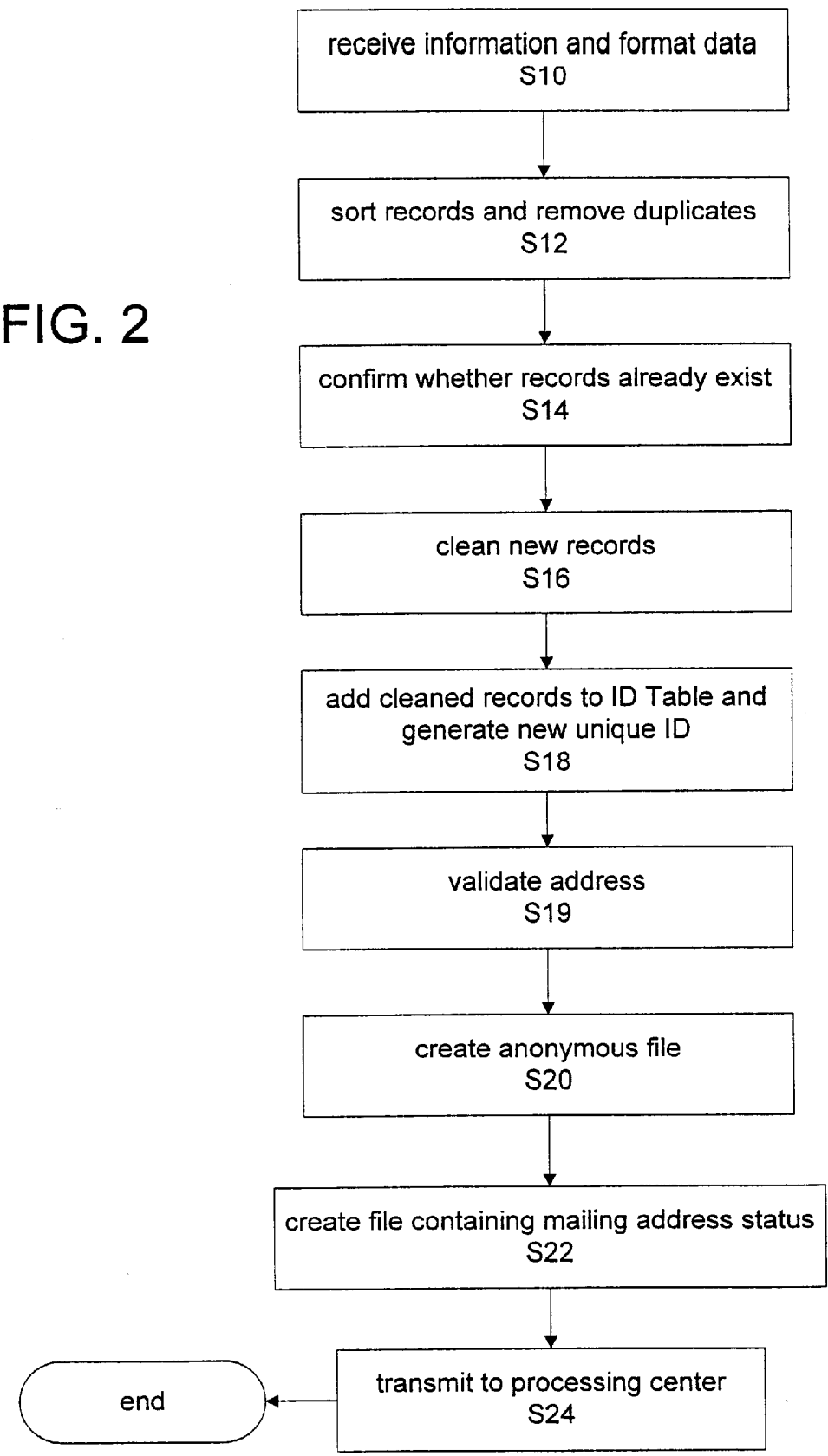
FIG. 2 shows an exemplary flow diagram of logic that executes on an on-site server to prepare data for transmission to a processing center, according to an aspect of the present invention.

The prescription information may include the number of refills prescribed, the number of refills remaining, the refill number, the date the prescription was dispensed, the quantity dispensed, the price of the prescription, the amount the patient paid for the prescription, the co-payment amount, the number of days supply dispensed, and dosing instructions. In a preferred embodiment the number of refills prescribed, the number of refills remaining, the refill number, the date dispensed, the quantity dispensed, and the days supply dispensed are required fields. Of course other information can be included. Referring now to FIG. 2, an exemplary process that executes on the on-site server 12, before processing by the data processing server 14, is now described.

A database program is required to be operating on the on-site server 12. According to a preferred embodiment, the database program is Microsoft SQL version 6.5 or higher, but any database would suffice. In order to load the received data into the database, a Bulk Copy Program (BCP) utility, available from Microsoft Corporation, can be run. Alternatively, the data may be received in the specified SQL-type format, or the data can be entered manually. Thus, after the data is received from the mainframe 10, the data is placed into the database at step S10.

At step S12 the records are sorted by first name, last name, address, city, and state. After sorting, duplicates are deleted. A duplicate is any person having the same first name, last name, and address. The records are sorted and the duplicates are deleted in order to determine whether the record represents a new patient. Thus, at step S14 the records are compared with a master ID table containing all patients previously processed to determine whether the patient is new.

If the patient is not in the master ID table the patient's record is cleaned at step S16. Cleaning the record includes searching for undesirable words, such as profanity, and searching for stray characters. The fields searched are the name fields and the address fields. Stray characters are deleted from a field. If an undesirable word is found, the data in the field is replaced with blank characters. According to a preferred embodiment, some undesirable words are: mother, father daughter, etc. These words result when a prescription is filled by the mother, father, daughter, etc. of the patient. Numbers are also deleted from selected fields, i.e., fields other than street address and zip code. The cleaned fields and the original fields are saved.

The record, including the cleaned fields, is inserted into the master ID table at step S18. At this time, a new unique ID is generated and is inserted into the record. A preferred method of generating unique IDs is to select the next sequential number. Alternatively, the unique ID could comprise the patient's initials followed by a three digit number, also generated sequentially. For example, John Smith would be assigned to JS001. If another John Smith, or a Jean Smythe is encountered, the unique ID would be JS002 and JS003, respectively.

Another way to generate the unique ID would be to employ random numbers. According to this system, random numbers are generated and assigned to each patient. After each random number is generated, the random number is verified to insure that it is unique. That is, the new random number is compared with all previous IDs to guarantee that the new random number is a unique ID.

Subsequently, at step S19 all of the address fields are analyzed to determine whether all fields are present. That is, step S19 identifies records that may not have correctly formatted data, for purposes of reporting to the pharmacy chain or other data owner or originator those records that should be corrected. If any of the address fields are blank, a flag is set indicating that the mailing address is invalid.

After the address is validated, at step S20 an anonymous file is created including all of the prescription information and the corresponding generic ID. All personal information, such as the patient's name and address, are not included in this new anonymous file. Consequently, anyone viewing this new anonymous file should not be able to identify the patient that originated the record.

The address validity flag is then inserted into a new "correction" file that contains the indication and the generic ID at step S22. Alternatively, the flag can be inserted into a field within the individual record. Thus, if all of the fields are present an indication that the mailing address is valid is inserted into the field or separate "correction" file. Finally, at step S24 the file containing the records having the substituted generic ID and the mailing address validity indication (either in a field within the file or in a separate file) are transmitted to the processing center and the program terminates execution.

Figure 3:
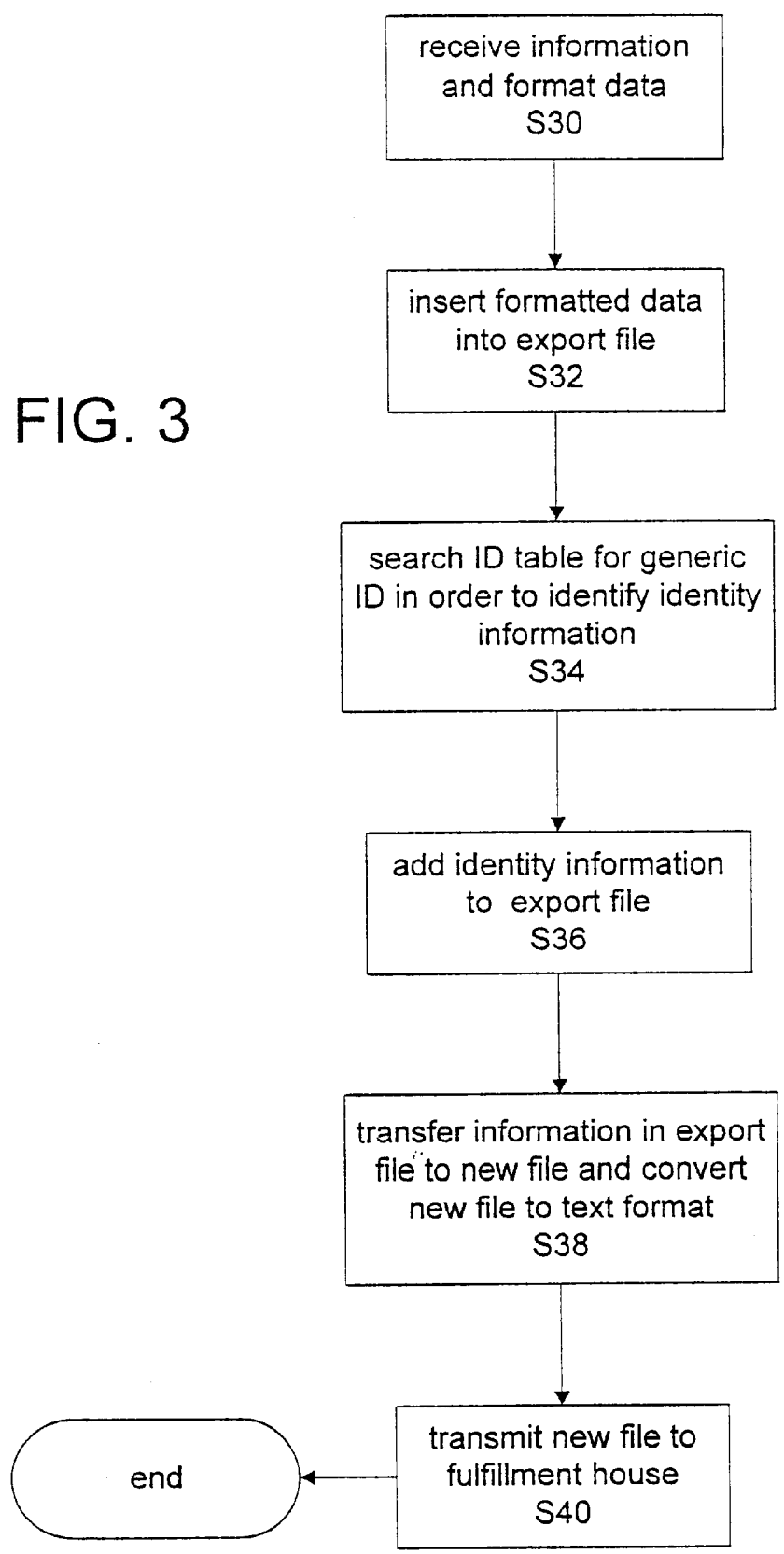
FIG. 3 show an exemplary flow diagram of logic that executes on an on-site server after processing by the processing center, according to an aspect of the present invention.

Referring to FIG. 3 an exemplary process that executes on the on-site server 12, after processing by the data processing server 14, is now described. Initially at step S30 data is received from the data processing center. The data includes several fields that indicate what type of intervention is necessary and the content of the letter the patient is to receive. An exemplary intervention type is reminding the patient that the prescription is expected to run out in the near future and that the patient should be refilling the prescription soon. The data arrives in a fixed length text file. Thus, the flat text files are moved into a SQL table using the BCP utility. The BCP utility uses the default export format file to load the text data into a SQL database table at step S32.

After creating the export table, at step S34 the ID table is searched using the generic IDs as search keys. When each generic ID is found, the corresponding identity information is identified and input into the export table at step S36. Preferably, the identity information includes the patient's first name, the patient's last name, and the patient's address. The process repeats until each generic ID in the export table is associated with its corresponding identity information.

Once the export table contains all the necessary identity information, a new text file is created at step S38. The new file contains all of the information from the export table including the identity information and the intervention information. Finally, at step S40 the new file is transmitted to the fulfillment house 16 so that the appropriate correspondence can be generated and mailed. Preferably, the fulfillment house 16 verifies the addresses, prints the letters, insert the letters into envelopes, and adds any additional inserts that may be required. Ultimately, the letter is mailed.

Alternatives to mailing the correspondence include faxing, and/or emailing the correspondence, and/or telephoning the patient, and/or paging the patient. If an alternate is utilized in lieu of or in addition to mail, the appropriate information must be included in the initial data sent to the on-site server 12. Obviously the additional information includes at least the patient's facsimile telephone number, and/or the patient's email address, and/or the patient's telephone number, and/or the patient's pager telephone number.

Figure 4:
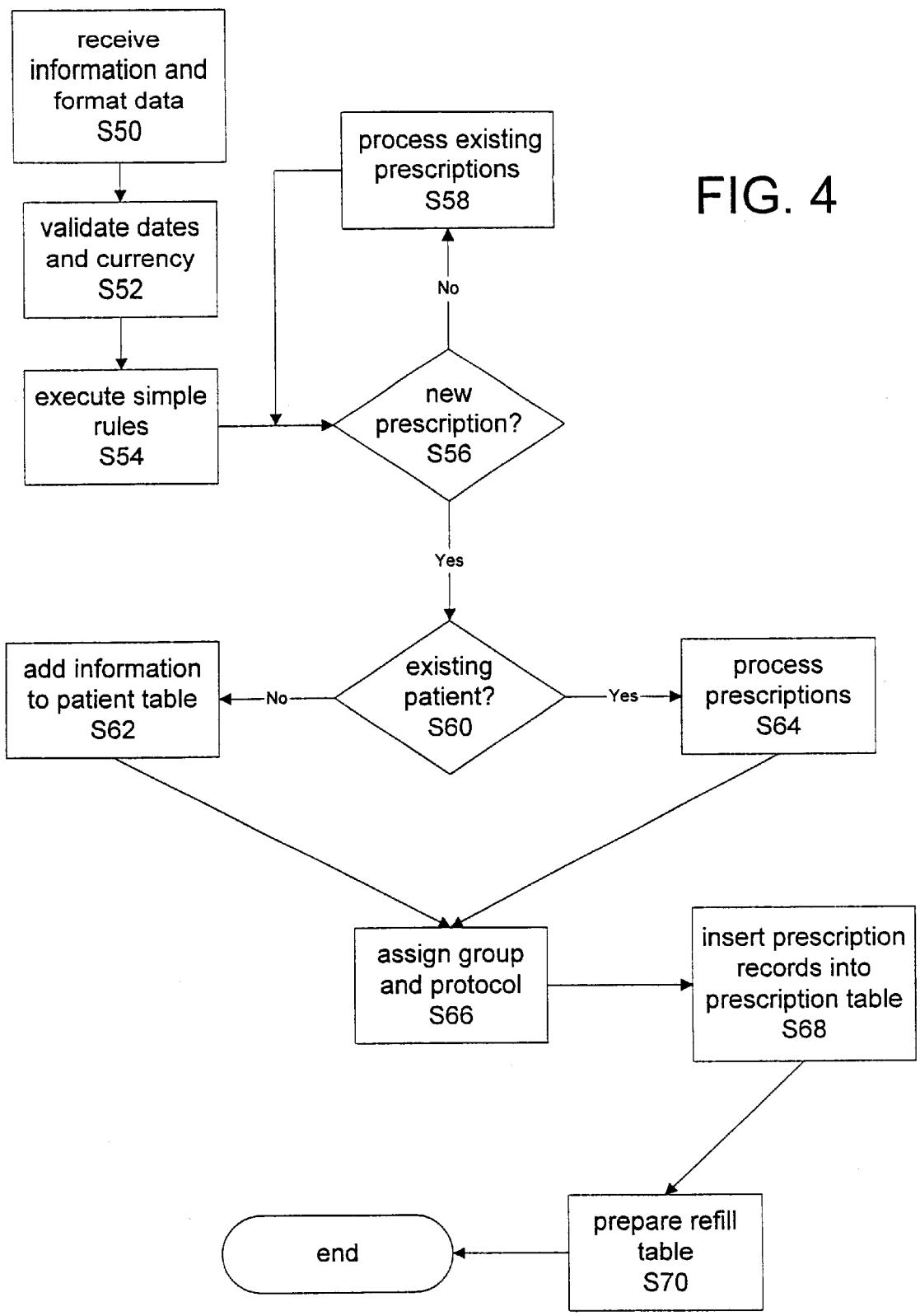
FIG. 4 show an exemplary flow diagram of logic that executes on a data processing server at the processing center during data importing, according to an aspect of the present invention.
Figure 5:
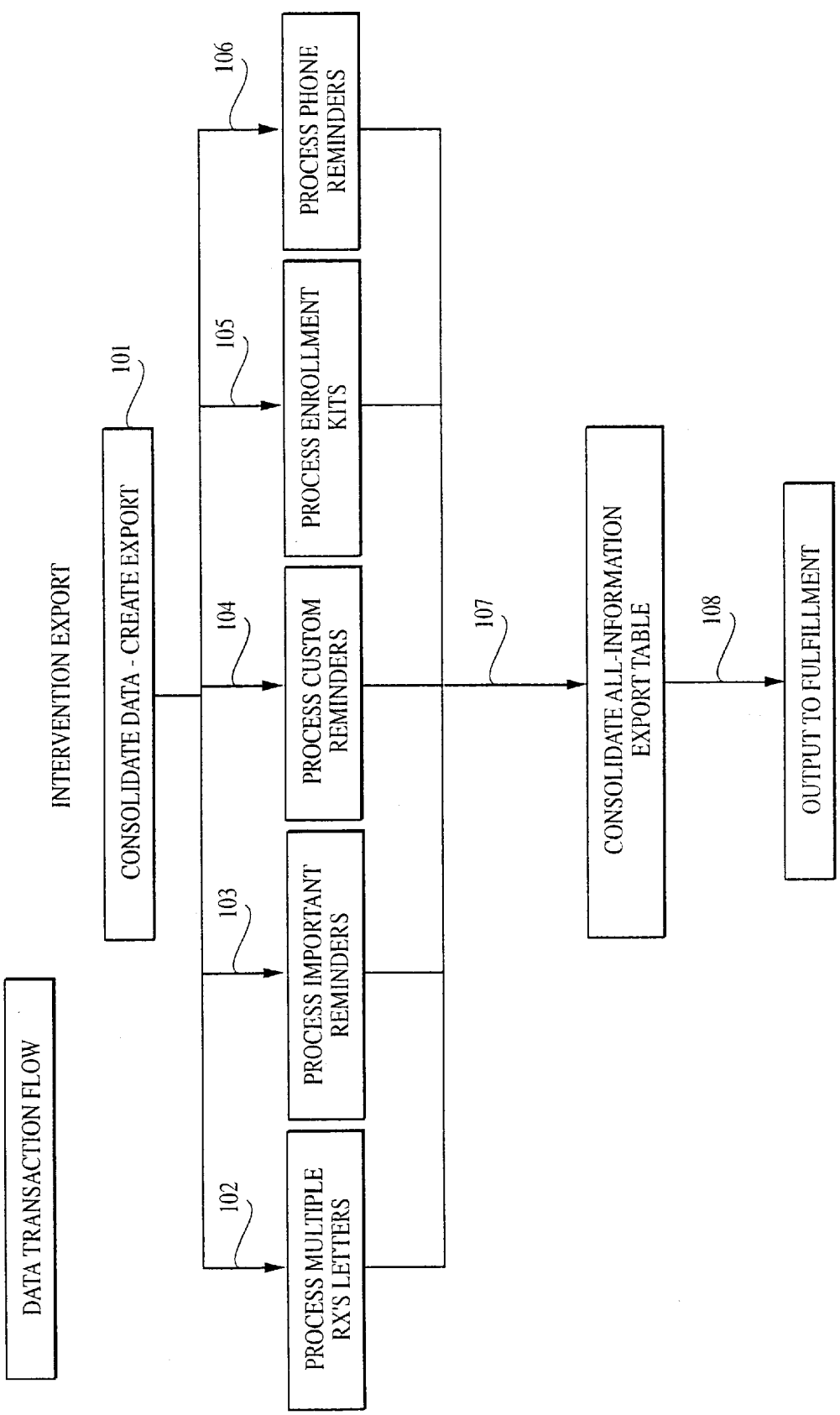
FIG. 5 show an exemplary flow diagram of additional logic that executes on the data processing server during data exporting, according to an aspect of the present invention.

Referring now to FIGS. 4 and 5, exemplary processes that execute on the data processing server 14 are now described. The following describes one type of data analysis that can be performed on the prescription data (e.g., on the matched substantive information and generic or anonymous identity information).

Initially, at step S50 data is received from the on-site server 12. The data may be transferred via tape transfer, modem or FTP. The data arrives in a fixed length text file. Thus, the flat text files are moved into an SQL format using the BCP utility. The BCP utility uses the default import format file to load the text data into a SQL database table.

Next, at step S52 a pre-processor is run against the data to check prescription dispense dates and currency values to see if they are in valid formats. For example, the currency values must be integer, i.e., without decimal points and the dates should be in a known format, such as day, month, year.

At step S54 the data is checked to see if it complies with simple rules. Simple rules include analyses such as confirming whether a drug is in a compliance program, checking whether the pharmacy that issued prescription is a valid pharmacy, checking the duration of a prescription, and checking whether any refills have been prescribed for the prescription.

A drug is in the compliance program if it is a selected drug. In other words, not all drugs need a compliance program. A pharmacy may be invalid if the pharmacy has ceased doing business. Such a pharmacy may have been entered due to a data entry error. The duration of the prescription is monitored to make sure that the prescription is not extremely short or long. For example, it may take ten days to receive the first intervention, thus making any prescription for less than ten days irrelevant to the compliance program. Similar reasoning applies to prescriptions without any refills. In a preferred embodiment, all prescriptions are ignored if the prescription is for less than twenty one (21) days and longer than one hundred eighty (180) days. Records having errors are moved into the error table that can be exported to a text file using the BCP utility.

At step S56 it is determined whether the prescription record is for a new prescription or for a refill of an existing prescription. If the record is for a refill of a prescription known to the system, at step S58 the refill table and prescription table are updated with the refill information and the next refill due date is calculated. For example, the number of refills remaining is reduced by one.

If the record is for a refill of a prescription unknown to the system, at step S60 the NDC and pharmacy status are validated. It is also determined whether the patient is known to the system. If the patient is not known to the system, at step S62 patient information is added to a patient table. Exemplary information includes the gender and age of the patient, as well as the date the patient is first registered into the system and the zip code of the patient's address.

If at step S60 it is determined that the patient is already an existing patient, the prescription is processed at step S64. Processing includes checking whether the new prescription is a substitute for an existing prescription. If the new prescription is a substitute, the prior prescription is suspended so that no more interventions will be sent based on the old prescription.

After steps S62 and S64, at step S66 the patient is assigned to a group and a protocol. Groups are based on at least the specific drug and may also be based on a combination of drug, age, gender, and geographic location. If the patient is an existing patient, at this step it is confirmed that the patient is in the same group when the new prescription is for the same drug as the previous prescription.

After the group is assigned, the patients are segmented into control group and non-control group. Patients in a control group receive no interventions and are used as a baseline to measure the effectiveness of the program. A patient is randomly assigned to a control group based on a ratio determined by the drug type. For example, drug A patients may have ten percent (10%) assigned to the control group, while drug B patients may have fifteen percent (15%) assigned to the control group. After the control group assignment, the non-control patients are assigned to a protocol. A protocol is the definition of the series of interventions the patient is to receive and is predetermined. There can be any number of protocols assigned to a group. If the patient is an existing patient, at this step it is confirmed that the patient has been assigned the same protocol, when the new prescription is for the same drug, as the previous prescription.

Subsequent to steps S66, all prescription records are inserted into a prescription table at step S68, and the refill table is prepared to accept future refills at step S70. Preparation of the refill table includes, for example, determining whether the prescription is a first time pick up. If it is a first time pick up, the refills number is set to zero. Then, the due date refill number one is calculated, thus indicating when a reminder should be triggered. In addition, it is monitored whether the refill has been picked up. The monitoring is performed by reviewing subsequent data transmissions. If the refill is not picked up, another reminder may be sent. After step S70 the import process is complete.

In FIG. 5, at step S101 the export file that will be sent back to the on-site server and ultimately the fulfillment house is consolidated. At this time, information is stored in a pre-export table. The information excluded includes dormant pharmacies, dormant NDCs, completed prescriptions, prescriptions determined to have a bad address, patients who have elected not to participate in the program, patients in the control group, and prescriptions that have been suspended. The prescriptions are linked to their associated refill information stored in the refill table. The export table is populated one batch at a time from the information in the pre-export table. Steps S102–S106 describe exemplary batches.

At step S102 the first batch is processed. The first batch includes all drugs that can be grouped with other drugs in a reminder letter. The prescriptions are due to be filled within the next 30 days. Thus, any prescription satisfying this criteria will have a record added to the export table. The record contains all the information necessary for the fulfillment house 16 to generate an intervention.

At step S103 the second batch is processed. The second batch includes all prescriptions that are past due for a refill. A system parameter determines how many days late a refill must be before an intervention is generated. The parameter varies by drug. The intervention is a reminder that the refill is overdue and how important it is to continue therapy as the doctor prescribed.

Custom reminders are processed next at step S104. A custom reminder is generated X days before a refill is due, with X varying from drug to drug. The reminder reinforces the importance of continuing therapy and that the current supply of drugs is due to be refilled soon. If the refill due is the last refill for the prescription, a reminder is added to visit the doctor to get a new prescription.

At step S105 new prescriptions are processed. After a patient picks up the prescription, an enrollment kit is mailed. The enrollment kit provides general information about the program, gives the patient a chance to decline participation, and provides information about the drug.

If the protocol requires a telephone call as an intervention, an export record is created at step S106. The export record is flagged as a telephone intervention.

After all of the batches are processed, at step S107 all of the information is consolidated into a text file using the BCP utility. The final file includes interventions dictated by the protocol for each prescription that was assigned during the import process. The final file is exported to the fulfillment house 16 via the on-site server 12 at step S108.

Because an object of the invention is to preserve patient confidentiality, access to the on-site server and to the data stored on the on-site server is restricted by a login routine. Three levels of security are required in a preferred embodiment, although more or fewer levels can be provided. The first level is for the local operator, the second level is for the remote operator, and the third level is for the data administrator. The local operator has authority to control the overall function and operation of the system, but does not have access to the data. The remote operator will often wish to administer the system from a remote site via the VPN and has the same access privileges. Only the data administrator has the ability to access the data. All access to the system or the data is recorded in system access logs. Additionally, any access to the data is recorded in database access logs.

Although the preceding description refers to the data processing center as being remote from the on-site server, the data processing center can also be located at the same site as the on-site server. Furthermore, the data processing can occur on the on-site server, such as with two different storage devices having different levels of access to preserve the confidentiality. As long as confidentiality is maintained, the present invention is applicable. In addition, although the fulfillment house is described as a separate entity, the on-site server can perform all of the functions of the fulfillment house transmitting all form letters that need to be sent in the form of a letter library, obviating the need for the fulfillment house. Thus, the server can merge the patient's identity information with the form letters and send the letters themselves. Such a configuration is still within the purview of the present invention.

Similarly, although the description refers to formatting the data manually, the procedure can be automated. For example, the system can detect when new data has arrived. According to this scenario, the arrival of the data triggers the whole import process such that the resulting files are automatically transmitted.

It is noted that the foregoing examples have been provided merely for the purpose of explanation and are in no way to be construed as limiting of the present invention. While the present invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the present invention in its aspects.

Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A method for facilitating compliance while maintaining a patient's confidentiality within a pharmaceutical system that includes an organization having a plurality of local systems and a local server; a remote compliance system; and a fulfillment system, the method comprising:

transferring a patient's identity information along with a patient's prescription information within the organization from the plurality of local systems to the local server;

substituting the patient's identity information with a unique generic ID at the local server;

transferring the generic ID and prescription information to the remote compliance system;

processing the prescription information associated with the generic ID to obtain intervention information by determining whether the prescription information is for a new prescription and, if the prescription information is for a new prescription, using the generic ID to determine whether the prescription information is for an existing patient;

exporting the intervention information, the generic ID, and a letter library to the local server;

retaining the identity information within the organization while transferring and processing the prescription information;

retrieving the patient's identity information using the generic ID at the local server;

merging the exported intervention information, letter library and the patient's identity information to obtain fulfillment information; and transferring the fulfillment information to the fulfillment system to generate correspondence to be sent to the patients;

wherein the patient's identity information is not transmitted to the remote compliance system.

2. The method of claim 1, in which the supplementing further comprises storing the patient's identity information and the generic ID in a table residing on the local server;

and in which the supplementing further comprises locating the unique ID in the table to find the corresponding patient's identity information.

3. The method of claim 1, in which the local server and the remote compliance system are located at the same site.

4. A system for processing data including specific identity information and corresponding substantive information, the system permitting analysis of the substantive information to occur while maintaining the confidentiality of a person identified by the specific identity information, the system comprising:

a data processor; and a server, within an organization, that stores the data and transmits the data to the data processor, the server substituting the specific identity information with unique generic identification information before transmitting so that the specific identity information is not transmitted to the data processor;

wherein the data processor imports the data, including the substituted generic identification information, and analyzes the substantive information to obtain results by determining whether the substantive information is an update for an existing record and, if the substantive information is not an update for an existing record, determining, using the substituted generic identification information, whether the data processor has an existing record for the person, the data processor exporting the results along with the associated generic identification information back to the server;

wherein the server associates the generic identification information with the corresponding specific identity information so that the results are associated with the specific identity information corresponding to the substantive information; and wherein the data processor analyzes the data without receiving the specific identity information and the specific identity information is retained within the organization while the data processor imports the data and analyzes the substantive information, thus maintaining confidentiality within the organization.

5. The system of claim 4, in which the specific identity information comprises a name and an address.

6. The system of claim 4, further comprising a local system within the organization that supplies the data to the server.

7. The system of claim 4, in which the results comprise intervention types and timing.

8. The system of claim 7, which the server receives the results and adds a name and address to the results so that correspondence can be generated in accordance with the intervention types and timing for the name.

9. The system of claim 8, in which the results, including the specific identity information, are forwarded from the server to a fulfillment house.

10. A system for processing data including specific identity information and substantive information, the system permitting analysis of the substantive information to occur at a remote site while maintaining the confidentiality of a person identified by the specific identity information, the system comprising:

a local server, within an organization, the local server storing the data and transmitting the data from the organization to the remote site, the local server substituting the specific identity information with unique generic identification information before transmitting; and an analyzing system residing at the remote site; the analyzing system importing the data, including the substituted generic identification information, from the local server and analyzing the substantive information to obtain results by determining whether the substantive information is an update for an existing record and, if the substantive information is not an update for an existing record, determining, using the substituted generic identification information, whether the analyzing system has an existing record for the person, the analyzing system exporting the results, along with the associated generic identification information, back to the local server of the organization;

wherein the specific identity information is not transmitted from the organization to the analyzing system and is retained within the organization while the analyzing system imports the data and analyzes the substantive information; and wherein the specific identity information is retrieved using the generic identification information so that the results are associated with the specific identity information corresponding to the substantive information.

11. The system of claim 10, in which the data is transmitted via a T1 connection.

12. The system of claimed 10, in which the specific identity information comprises a patient's name and address.

13. A system for processing data including specific identity information and substantive information, the system permitting analysis of the substantive information to occur at a remote site while maintaining confidentiality of a person identified by the specific identity information, the system comprising:

a server, within an organization, the server storing the data and transmitting the data, the server substituting the specific identity information with unique generic identification information before transmitting; and an analyzing system residing at the remote site, the analyzing system receiving the transmitted data, including the substituted generic identification information, and analyzing the substantive information to obtain results by determining whether the substantive information is an update for an existing record and, if the substantive information is not an update for an existing record, determining, using the substituted generic identification information, whether the analyzing system has an existing record for the person, the analyzing system exporting the results along with the associated generic identification information back to the server;

wherein the server retrieves the specific identity information using the generic identification information so that the results are matched with the specific identity information corresponding to the substantive information that is the source of the results; and wherein the specific identity information is not transmitted from the server to the analyzing system and is retained within the organization while the analyzing system receives the data and analyzes the substantive information.

14. A method for processing data including specific identity information and substantive information, the system permitting analysis of the substantive information to occur while maintaining the confidentiality of a person identified by the specific identity information, the method comprising:

storing the data within a server of an organization;

substituting the specific identity information with unique generic identification information; and transmitting the data, including the substituted generic identification information and the substantive information, from the server to a data processor;

importing the data to the data processor, including the substituted generic identification information, and analyzing the substantive information to obtain results by determining whether the substantive information is an update for an existing record and, if the substantive information is not an update for an existing record, determining, using the substituted generic identification information, whether the data processor has an existing record for the person;

retaining the specific identity information within the organization while the data processor imports the data and analyzes the substantive information;

exporting the results along with the associated generic identification information back to the server;

associating the generic identification information with the corresponding specific identity information at the server so that the results are associated with the specific identity information corresponding to the substantive information that is the source of the results;

wherein the data processor does not receive the specific identity information from the organization.

15. The method of claim 14, wherein the server transmits the results to a fulfillment house.

16. The method of claim 14, wherein the server processes the results and transmits correspondence in accordance with the results.

17. The method of claim 14, wherein the server cleans the data before transmitting the data to the data processor.

18. The method of claim 17 wherein the server cleans the data by removing undesired predetermined information from the data before transmitting the data to the data processor.

19. The method of claim 14, wherein the server and the data processor are located at the same site.

20. The method of claim 14, wherein the server and the data processor are located at different sites.

21. A medical data analysis preparation system for processing prescription data including personal identity information and prescription information and for preventing access to the personal identity information by a data processor that analyzes the prescription information, the system comprising:

a classification component, executed by a server within an organization that classifies records of the prescription data into the personal identity information and the prescription information while maintaining association of the personal identity information with the prescription information;

an anonymizing component, executed by the server within the organization that converts at least one predetermined field within the personal identity information to unique generic identification information associated with the prescription information;

a confidential data stripping component, executed by the server within the organization that removes all personal identity information from the prescription data other than the generic identification information;

a transmitting component that transmits the prescription information, together with the associated generic identification information, from the organization to the data processor;

a receiving component for receiving analysis results, along with the associated generic identification information, from the data processor, the analysis results including processed results obtained by determining whether the prescription information is related to an existing record at the data processor and, if the prescription information is not related to an existing record, determining whether the prescription information is for an existing patient using the generic identification information;

an associating component, executed by the server within the organization, that associates the generic identification information with corresponding personal identity information and converts the at least one predetermined field back into the personal identity information; and an output component that outputs the analysis results together with the associated personal identity information;

wherein the personal identity information is not transmitted from the organization to the data processor and the personal identity information is retained within the organization when the transmitting component transmits the prescription information to the data processor.

22. The system of claim 21, in which the personal identity information comprises a name and an address.

23. The system of claim 21, further comprising:

an intervention action component that converts the analysis results into intervention types and timing associated with the personal identity information and generates preformatted letters.

24. A system for processing data including specific identity information and substantive information, the system permitting analysis of the substantive information to occur while maintaining the confidentiality of a person identified by the specific identity information, the system comprising:

a server, within an organization, stores the data and transmits the data, the server substituting the specific identity information with unique generic identification information before transmitting to a data processor;

wherein the server receives results along with the associated generic identification information, and then associates the generic identification information with the corresponding specific identity information so that the results are associated with the specific identity information corresponding to the substantive information that is the source of the results, the results being obtained by determining at the data processor whether the substantive information is an update for an existing record at the destination outside of the organization and, if the substantive information is not an update for an existing record, determining, using the substituted generic identification information, whether the data processor has an existing record for the person; and wherein specific identity information is not transmitted to the data processor and is retained within the organization when the data is transmitted to the data processor.

25. The system of claim 24, in which the server resides at a pharmacy.

* * * * *

UNITED STATES PATENT AND TRADEMARK OFFICE
CERTIFICATE OF CORRECTION

PATENT NO. : 6,654,724 B1
DATED : November 25, 2003
INVENTOR(S) : D. Rubin et al.

It is certified that error appears in the above-identified patent and that said Letters Patent is hereby corrected as shown below:

Column 17,
Line 18, before "stores" insert -- that --.

Column 14,
Line 33, before "which" insert -- in --.

Column 15,
Line 10, "claimed" should be -- claim --.

Column 18,
Line 16, before "data processor" should be -- destination outside of the organization --.

Signed and Sealed this

Twenty-first Day of September, 2004

JON W. DUDAS
*Director of the United States Patent and Trademark Office*